United States Patent [19]

Kawamura

[11] Patent Number: 5,183,050
[45] Date of Patent: Feb. 2, 1993

[54] PULSE WAVE SENSOR

[75] Inventor: Norio Kawamura, Nagoya, Japan

[73] Assignee: Colin Electronics Co., Ltd., Aichi, Japan

[21] Appl. No.: 790,354

[22] Filed: Nov. 12, 1991

[30] Foreign Application Priority Data

Apr. 16, 1991 [JP] Japan ................... 3-34295[U]

[51] Int. Cl.$^5$ ................................ A61B 5/02
[52] U.S. Cl. ...................... 128/687; 128/672; 128/690
[58] Field of Search ............ 128/644, 670-672, 128/677-683, 686-690

[56] References Cited

U.S. PATENT DOCUMENTS

| 4,830,017 | 5/1989 | Perry et al. | 128/687 |
| 4,901,733 | 2/1990 | Kaida et al. | 128/687 |
| 4,951,679 | 8/1990 | Harada | 128/687 |
| 4,987,900 | 1/1991 | Eckerle et al. | 128/687 |
| 5,103,831 | 4/1992 | Niwa | 128/687 |
| 5,119,822 | 6/1992 | Niwa | 128/687 |
| 5,131,400 | 7/1992 | Harada et al. | 128/690 |

Primary Examiner—Randall L. Green
Assistant Examiner—R. Clarke
Attorney, Agent, or Firm—Oliff & Berridge

[57] ABSTRACT

A pulse wave sensor for detecting a pressure pulse wave produced from an arterial vessel of a living subject in synchronism with heartbeat of the subject, the sensor having a press surface adapted to be pressed on a body surface of the subject over the arterial vessel, the sensor including (a) a protruding portion protruding from the press surface, the protruding portion having a top surface adapted to be pressed on the body surface of the subject, (b) a sensing device provided in the top surface of the protruding portion, for detecting the pressure pulse wave from the arterial vessel via the body surface, and (c) a sheet spring provided around the protruding portion and having a height generally equal to, or greater than, a height of the protruding portion as measured from the press surface, the sheet spring being deflectable in a direction in which the top surface of the protruding portion is pressed on the body surface.

8 Claims, 2 Drawing Sheets

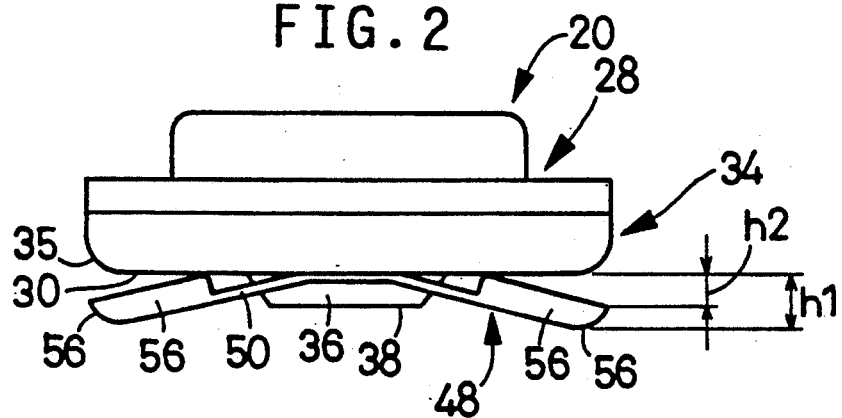
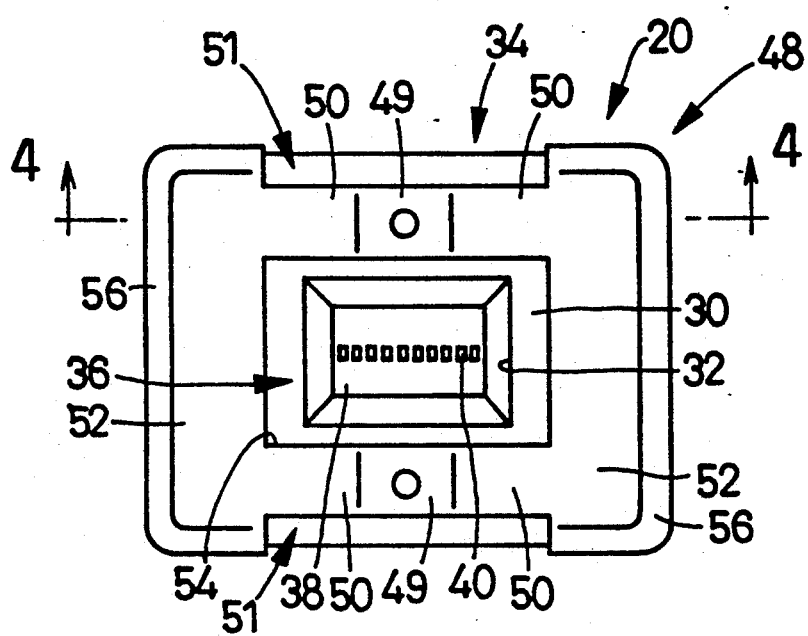
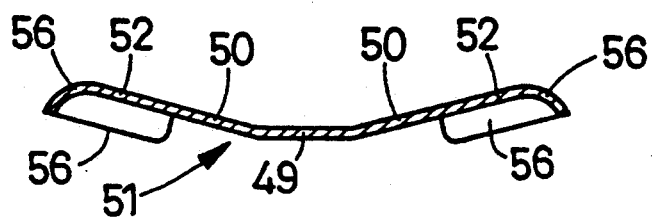

PULSE WAVE SENSOR

BACKGROUND OF THE INVENTION

1. Field of the Invention

The present invention relates to a pulse wave sensor for detecting pressure pulse wave from an artery of a living subject.

2. Related Art Statement

There is known a pulse wave sensor having a press surface adapted to be pressed on a body surface of a subject, a protruding portion protruding from the press surface, and pressure sensing means provided in a top surface of the protruding portion. An example of this sensor is disclosed in U.S. Pat. No. 4,901,733 published on Feb. 20, 1990, the Assignee of which is the Assignee of the present application. When the protruding portion is pressed on the body surface over a superficial artery such as radial artery or dorsal artery of foot, the pressure sensing means detects pressure pulse wave produced in the artery in synchronism with heartbeat of the subject. Although in many cases bone and tendon occur near a superficial artery from which pressure pulse wave is to be detected, the pressure sensing means provided in the top surface of the protruding portion appropriately is pressed against the artery without being interfered by the tendon or bone.

In order to measure pressure in an artery (i.e, blood pressure) as accurately as possible by detecting pressure pulse wave from the artery, it may be required that the pulse wave sensor be pressed on the body surface with an optimum pressing force which causes the wall of the underlying artery to partially be flattened. If, to this end, the height of the protruding portion as measured from the press surface is selected at a small value to suitably press an artery shallow under body surface, then this arrangement is not suitable for a deep artery, because the sensor must be pressed with an excessively great force for overcoming resistance or interference between the other portion of the press surface than the protruding portion, and the bone and/or tendon near the artery. This results in causing the subject to feel discomfort or even pain. In addition, the sensor may fail to establish an optimum pressing force which partially flattens the artery. On the other hand, if the height of the protruding portion is selected at a great value to suitably press a deep artery, then the arrangement is not suitable for a shallow artery, because the sensor must be pressed with a small force as an optimum pressing force. In this case, the other portion of the press surface than the protruding portion does not contact the body surface. Thus, the sensor takes an unstable posture or position, and therefore the sensor does not detect pressure pulse wave with stability. Since the depth of a superficial artery such as radial artery or pedal dorsal artery finds differences among individual subjects, a predetermined height of the protruding portion of the pulse wave sensor may cause some subjects to feel discomfort, may fail for some subjects to establish an optimum pressing force, and may not stably detect pressure pulse wave from other subjects.

In the above-identified background, the Assignee of the present application proposed, in Japanese Utility Model Application No. 2-46420 filed Apr. 27, 1990, to provide a soft deformable member, such as a compressed deformable rubber, around a protruding portion on a press surface of a pulse wave sensor. The soft deformable member has a height generally equal to, or greater than, that of the protruding portion. When the protruding portion presses a deep artery via body surface, the soft deformable member is deformed by compression thereof between the press surface and the body surface, so that the protruding portion protrudes from the level of the top of the deformed member by an amount or distance corresponding to the depth of the artery. This arrangement appears to eliminate the above-indicated problems with the first pulse wave sensor.

However, even the second pulse wave sensor is not satisfactory, because the amount of compressed deformation of the soft deformable member (i.e., spring characteristic) is not linear with respect to load applied thereto. Therefore, for a deep artery, the soft deformable member does not easily produce a sufficient deformation, that is, does not easily cause the protruding portion to project therefrom by a sufficient amount corresponding to the depth of the artery. Therefore, an excessively great pressing force is applied to the sensor to establish an optimum pressing force which partially flattens the artery. Consequently, this sensor may cause the subject to feel discomfort due to the excessively great pressing force applied thereby.

SUMMARY OF THE INVENTION

It is therefore an object of the present invention to provide a pulse wave sensor including a protruding portion having pressure sensing means in the stop surface thereof, which sensor is pressed against an artery via body surface to establish an optimum pressing force, irrespective of the depth of the artery, and detect pressure pulse wave from the artery with stability, while preventing the subject from feeling discomfort due to the pressing.

The above object has been achieved by the present invention, which provides a pulse wave sensor for detecting a pressure pulse wave produced from an arterial vessel of a living subject in synchronism with heartbeat of the subject, the sensor having a press surface adapted to be pressed on a body surface of the subject over the arterial vessel, the sensor comprising (a) means for providing a protruding portion protruding from the press surface, the protruding portion having a top surface adapted to be pressed on the body surface of the subject, (b) sensing means provided in the top surface of the protruding portion, for detecting the pressure pulse wave from the arterial vessel via the body surface, and (c) a sheet spring provided around the protruding portion and having a height generally equal to, or greater than, a height of the protruding portion as measured from the press surface, the sheet spring being deflectable in a direction in which the top surface of the protruding portion is pressed on the body surface.

In the pulse wave sensor constructed as described above, the sheet spring which is deflectable in the direction in which the press surface is pressed on the body surface and has a height generally equal to, or greater than, that of the protruding portion, is provided around the protruding portion. With the protruding portion being pressed against an artery via body surface to detect pressure pulse wave from the artery, the sheet spring is pressed against bone and/or tendon located near the artery, so as to be elastically deflected, thereby causing the protruding portion to project a suitable length from the level of the top of the spring. If the height of the protruding portion is greater than that of a conventionally used protruding portion and the spring modulus of the sheet spring is selected at a small value, the sensor easily establishes, as an optimum pressing force which partially flattens the wall of the artery, a moderate pressing force even for a deep artery, since the sheet spring is easily elastically deflected and no interference occurs between the other portion of the press surface than the protruding portion and the bone and/or tendon near the artery. In this case, therefore, the sensor does not cause the subject to feel discomfort due to the pressing thereby. Meanwhile, for a shallow artery, the sheet spring is pressed against the bone and/or tendon, which assures that the sensor takes a stable posture on the body surface with respect to the underlying artery and therefore stably detects pressure pulse wave from the artery.

In addition, the spring characteristic of the sheet spring is linear. That is, the sheet spring is linearly deflected with respect to load applied thereto. In contrast to a soft deformable member which has a non-linear spring characteristic, such as a rubber member, the sheet spring provides a sufficient amount of deformation to establish an optimum pressing force even for a deep artery, without having to excessively increasing the pressing force. This results in more advantageously relieving the subject from discomfort or even pain. Thus, the present pulse wave sensor establishes an optimum pressing force, irrespective of the depth of an artery, and detects pressure pulse wave from the artery with stability, while effectively preventing the subject from feeling discomfort due to the pressing thereby.

According to a preferred feature of the present invention, the sheet spring includes at last one first portion and at least one second portion, the sheet spring being fixed at the first portion thereof to the press surface, the sheet spring being adapted to be pressed at the second portion thereof on the body surface of the subject, the second portion being deflectable relative to the first portion when being pressed on the body surface.

According to another feature of the present invention, the sheet spring has a window formed therethrough at a central portion thereof, the protruding portion protruding through the window, the at least one first portion consisting of two first portions spaced apart from each other by the window in a first direction parallel to the arterial vessel with the pulse wave sensor being pressed on the body surface, the at least one second portion consisting of two second portions spaced apart from each other by the window in a second direction perpendicular to the first direction.

According to yet another feature of the present invention, the sheet spring further includes two pairs of third portions, the two pairs being spaced from each other by the window in the first direction, the two third portions of each of the two pairs being continuous with a corresponding one of the two first portions located therebetween and with the corresponding ones of the two second portions, each of the two third portions of the each pair being bent from the corresponding one first portion at a predetermined angle with respect to the press surface.

According to a further feature of the present invention, the sheet spring further includes a curved portion extending from an outer periphery of each of the second portions toward the press surface, the press surface having a rounded outer periphery matched with a curvature of the two curved portions of the sheet spring, the two curved portions closely fitting over the rounded outer periphery of the press surface when the second and third portions of the sheet spring closely contact the press surface upon application thereto of an excessively large force between the press surface and the body surface.

In a preferred embodiment of the present invention, the pressure sensing means comprises a plurality of pressure sensing elements formed in an array extending in a direction perpendicular to the arterial vessel with the pulse wave sensor being pressed on the body surface.

In another embodiment of the present invention, the means for providing the protruding portion comprises (a1) a support member from which the protruding portion protrudes, the support member including a portion thereof adapted to be secured to a device which operates for pressing the pulse wave sensor against the arterial vessel via the body surface, and (a2) a cover member covering the support member to provide the press surface, the covering member having a window through which the protruding portion protrudes from the support member.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which:

FIG. 2 is an enlarged view of the pulse wave sensor of FIG. 1, showing a sheet spring in its free state;

FIG. 3 is a view of the pulse wave sensor of FIG. 1 as seen from the side of the sheet spring thereof; and FIG. 4 is a cross sectional view of the sheet spring of FIG. 3, taken along line 4—4 of FIG. 3.

DETAILED DESCRIPTION OF THE PREFERRED EMBODIMENT

Figure 1:
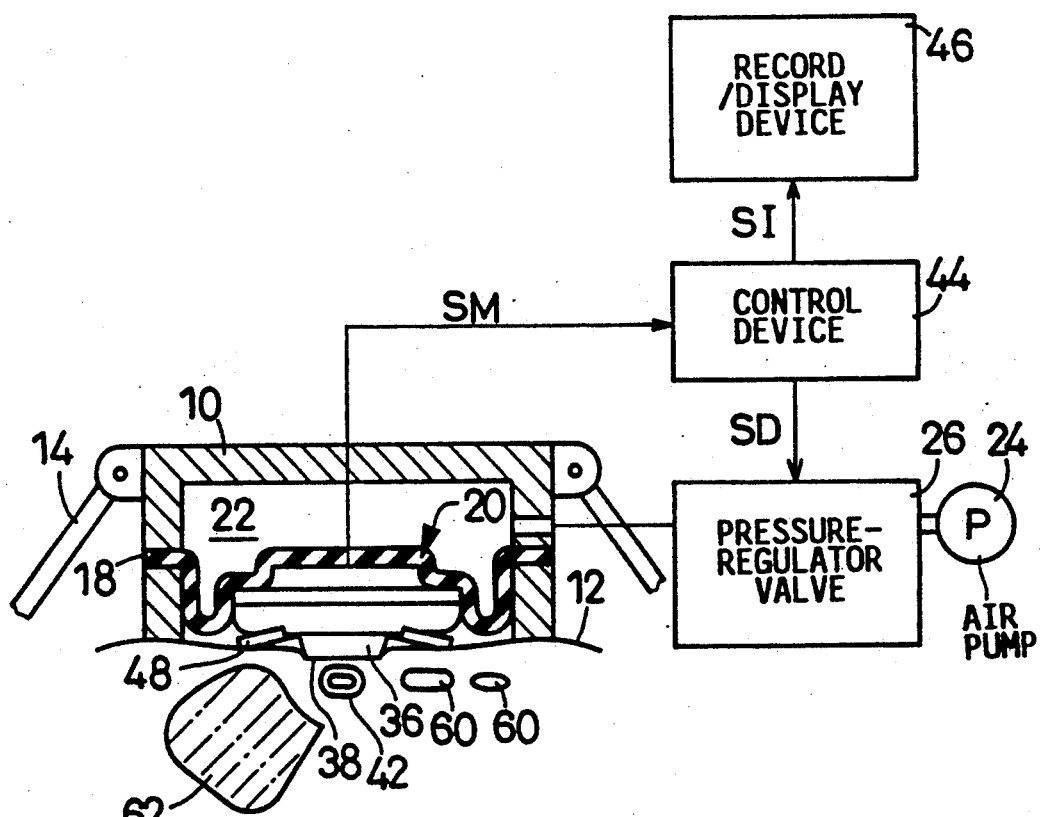
FIG. 1 is a view of a pulse wave sensor system to which the present invention is applied, showing the sensor being pressed with an optimum pressing force.

Referring first to FIG. 1, there is shown a pulse wave sensor system to which the present invention is applied. In the figure, reference numeral 10 designates a rectangular, box-like housing having a bottom wall and an opening. The housing 10 is detachably set on a wrist of a living subject with the help of belts or bands 14, such that the opening of the housing 10 contacts the skin or surface 12 of the wrist. A flexible diaphragm 18 is secured to the inner wall of the housing 10 to define a pressure chamber 22 inside the housing 10. A pulse wave sensor 20 is fixed to the outer surface of the diaphragm 18, so that the sensor 20 is advanceable out of the opening of the housing 10. The pressure chamber 22 is supplied with pressurized fluid, such as pressurized air, from an air pump 24 via a pressure-regulator valve 26. Thus, the pulse wave sensor 20 is adapted to be pressed on the body surface 12 with a pressing force corresponding to the air pressure in the chamber 22.

As shown in FIGS. 2 and 3, the pulse wave sensor 20 includes a support member in the form of a casing 28 made of a transparent resin, and a cover member 34 formed of a metal. The casing 28 is secured at an upper portion thereof (as seen in FIG. 2) to the diaphragm 18. The cover member 34 is fixed to a lower portion of the casing 28, and has a press surface 30 remote from the casing 28. A rectangular window 32 is formed through the cover member 34. The casing 28 includes a protruding portion 36 which protrudes from the lower portion of the casing 28 through the window 32 toward the opening of the housing 10, that is, toward the body surface 12 of the subject. The protruding portion 36 has a top surface 38 adapted to press the body surface 12. A plurality of semiconductor pressure sensing elements 40 are provided at regular intervals of, for example, 0.3 mm, in an array, in the top surface 38 of the protruding portion 36. With the housing 10 (or sensor 20) being set on the body surface 12, the array of sensing elements 40 extends in a direction perpendicular to the direction of extension of a radial artery 42 below the body surface 12 of the wrist (hereinafter, referred to as the "direction A"). With the pulse wave sensor 20 being pressed at the top surface 38 thereof against the radial artery 42 via the body surface 12, each of the pressure sensing elements 38 detects oscillatory pressure wave or pressure pulse wave produced in the radial artery 42 in synchronism with heartbeat of the subject and transmitted to the top surface 38 of the protruding portion 36 via the body surface 12, and generates an electric signal representing the detected pressure pulse wave (hereinafter, referred to as the pulse wave signal SM). The pulse wave signal SM is supplied to a control device 44.

The control device 44 includes a so-called microcomputer. The microcomputer processes input signals according to control programs pre-stored therein, so as to produce a drive signal, SD, to the pressure-regulator valve 26 and thereby regulate the pressure in the pressure chamber 22. In addition, the control device 44 (or microcomputer thereof) reads in the pulse wave signals SM supplied from the pressure sensing elements 38 of the pulse wave sensor 20 when the pressure in the chamber 22 is increased at a low rate, and determines, by utilizing the read in signals SM, an optimum pressing force (i.e., optimum pressure in the chamber 22) to be applied to the sensor 20. The wall of the radial artery 42 is partially flattened by the optimum pressing force applied thereto by the sensor 20. Further, by using the read in signals SM, the control device 44 selects, as an optimum pressure sensing element 40, one of the number of sensing elements 40 such that the optimum sensing element 40 provides a pulse wave signal SM having the greatest amplitude of the signal amplitudes provided by the sensing elements 40. The optimum pressure sensing element 40 rides directly above the center of the flattened wall of the radial artery 42. While the control device 44 controls the pressure-regulator valve 26 to maintain the optimum pressure in the chamber 22, the control device 44 concurrently reads in the pulse wave signal SM supplied from the optimum sensing element 40, and produces a record/display signal, SI, to a display/record device 46 so as to record and display the pressure pulse wave (waveform) represented by the read in optimum signal SM. The signal SM from the optimum sensing element 40 positioned right above the center of the flattened radial artery 42, is considered as being free from influences by elastic force (or tensile force) produced in the wall of the radial artery 42 at the time of distension thereof. Therefore, the waveform recorded and displayed by the record/display device 46 directly indicates the variation of blood pressure in the radial artery 42. In addition, the control device 44 determines, as a systolic and a diastolic blood pressure of the subject, an upper-peak and a lower-peak magnitude of each of pulses of the pulse wave signal SM supplied from the optimum sensing element 40, according to the pre-stored control programs, and commands the record/display device 46 to indicate the determined blood pressure values.

The height of the protruding portion 36 as measured from the press surface 30 is about 1.5 time as great as that (about 1 mm) of a conventionally used one. Thus, the pulse wave sensor 20 is suitable for a subject who has a radial artery 42 deep under body surface 12.

A flat or sheet spring 48 is provided around the protruding portion 36 and fixed to the press surface 30. As shown in FIG. 3, the sheet spring 48 is obtained by punching out a rectangular window 54 in a generally rectangular, sheet-like, thin metal material and bending the metal material having the window 54 at middle two portions 49, 49 thereof spaced from each other by the window 54. The thus obtained sheet spring 48 has a generally V-shaped cross section wherein the angle of inclination of each "wing" with respect to the press surface 30 is predetermined at a considerably small value. The above-indicated middle two portions 49, 49 serve as fixed portions 49, 49 to be fixed to the press surface 30 of the cover member 34 on both sides of the protruding portion 36. Each fixed portion 49 is continuous with two inclined portions 50, 50 on both sides thereof, and cooperate with the inclined portions 50, 50 to provide a V-shaped portion 51. The sheet spring 48 further includes a pair of contact portions 52, 52 spaced from each other by the window 54. The two contact portions 52 connect between the two V-shaped portions 51, 51 on both sides of the window 54. The sheet spring 48 is fixed at the fixed portions 49, 49 to the press surface 30 such that the fixed portions 49, 49 are opposite to each other in a direction perpendicular to the direction A in which the array of pressure sensing elements 40 extends, that is, parallel to the direction of extension of the radial artery 42. With the sheet spring 48 being fixed to the press surface 30, the protruding portion 36 protrudes through the window 54 of the sheet spring 48. The fixation of the fixed portions 49, 49 to the press surface 30 of the cover member 34 is effected by, for example, spot welding indicated at circles in FIG. 3.

In addition, the sheet spring 48 includes a curved portion 56 along the outer periphery of each of the contact portions 52, 52. The two curved portions 56, 56 serve for helping the corresponding contact portions 52, 52 in suitably pressing the body surface 12. The curved portions 56, 56 extend toward the press surface 30 of the cover member 34, and have positions and curvatures matched with those of a rounded outer periphery 35 of the press surface 30. Therefore, when the sheet spring 48 is pressed by an excessively large pressing force against the body surface 12, the contact portions 52, 52 deflect relative to the fixed portions 49, 49 and contact portions 52, 52 to the extent that the inclined portions 50, 50 become parallel to the press surface 30 and the curved portions 56, 56 closely fit over the rounded outer periphery 35 of the press surface 30.

The material, thickness, and spring modulus of the sheet spring 48, and the height in a free state of the sheet spring 48 relative to the height of the protruding portion 36, are so pre-determined that, for a subject who has a shallow radial artery 42 below body surface 12, the sheet spring 48 is pressed against a tendon 60 and/or a radius 62 via the body surface 12 and therefore the pulse wave sensor 20 continues to take a stable posture or position while the optimum pressing force simultaneously is maintained. Meanwhile, for a subject who has a deep radial artery 42, the sheet spring 48 in pressed contact with the tendon 60 and/or radius 62 via the body surface 12, is easily elastically deflected without having to excessively increase the pressure in the chamber 22, so that the wall of the radial artery 42 is partially flattened as shown in FIG. 1. The sheet spring 48 is formed of, for example, Stainless Steel SUS 301 having a thickness of about 0.15 mm. The spring modulus of the spring 48 is selected at a sufficiently smaller value than that of the tendon 60 or radius 62 and a sufficiently greater value than that of the wall of the radial artery 42. The height, $h_1$, of the sheet spring 48 (specifically, tops of the contact portions 52, 52) in the free state thereof as measured from the press surface 30 of the cover member 34 is comparatively greater than the height, $h_2$, of the protruding portion 36 from the press surface 30, as shown in FIG. 2.

As emerges from the foregoing description, the present pulse wave sensor 20 includes the sheet spring 48 which has a height greater than that of the protruding portion 36 and is deflectable in the direction of protrusion of the protruding portion 36, that is, direction in which the top surface 38 is pressed on the body surface 12. The sheet spring 48 is provided around the protruding portion 36. With the protruding portion 36 being pressed against the radial artery 42 via the body surface 12 for detecting the pressure pulse wave, the sheet spring 48 is pressed against the tendon 60 and/or radius 62 occurring near the radial artery 42 and is elastically deflected, so that the protruding portion 36 is advanced outward a suitable amount from the level of the tops of the contact portions 52, 52 of the deflected sheet spring 48. Since in the present embodiment the height of the protruding portion 36 is great and the spring modulus of the sheet spring 48 is small as described above, there will not arise the problem of interference between the press surface 30 and the tendon 60 and/or radius 62, even for a subject who has a deep radial artery 42. That is, the sheet spring 46 is suitably deflected without having to excessively increase the pressing force applied to the sensor 20, so that the radial artery 42 is partially flattened under an optimum pressing force that is not excessively or unnecessarily high. Thus, the pulse wave sensor 20 does not cause the subject to feel any discomfort due to the pressing thereby. In addition, the present sensor 20 enables the radial artery 42 to be pressed by the optimum pressing force, with high reliability. Furthermore, for a shallow radial artery 42, the sheet spring 48 is pressed against tendon 60 and/or radius 62 near the artery 42, so that the sensor 20 takes a stable posture relative to the body surface 12 or artery 42. Thus, the sensor 20 detects pressure pulse wave from the artery 48 with high stability.

The sheet spring 48 used in the present embodiment has a linear spring characteristic, that is, is linearly deflectable with respect to the pressing force applied thereto. Even in the case where the protruding portion 36 presses a deep radial artery 42, the sheet spring 48 is suitably deflected by an amount proportional to the pressing force applied thereto, that is, depth of the radial artery 42 as measured from body surface 12. Therefore, the radial artery 42 is partially flattened by an optimum pressing force which is considerably low. In contrast thereto, in a similar case, a soft deformable member which does not deform linearly is required to be pressed with an excessively great pressing force for providing a sufficient amount of deformation thereof to press a radial artery with an optimum pressing force. This results in causing the subject to feel discomfort or even pain.

In the present embodiment, the contact portions 52, 52 of the sheet spring 48 do not press an area on the body surface directly above the radial artery 42 but presses areas on the body surface away from the artery 42. Therefore, the pulse wave sensor 20 detects the pressure pulse wave with higher accuracy.

In addition, in the present embodiment, the sheet spring 48 is elastically deflectable to the extent that the V-shaped portions 51, 51 become flat on, and parallel to, the press surface 30 notwithstanding that the contact portions 52, 52 are provided with the curved portions 56, 56. Accordingly, the height of the protruding portion 36 protruding from the press surface 30 is not unnecessarily increased.

While the present invention has been described in its presently preferred embodiment, the present invention may otherwise be embodied.

For example, while in the illustrated embodiment the height of the sheet spring 48 from the press surface 30 is considerably higher than that of the protruding portion 36, it is possible that the sheet spring 48 be slightly higher than, or slightly shorter than, the protruding portion 36. In this case, the sheet spring 48 provides the same advantages as described above. In short, the present invention requires that the sheet spring 48 have a height generally equal to, or greater than, that of the protruding portion 36.

In the illustrated embodiment, the sheet spring 48 is adapted to contact the body surface 12 such that the pair of contact portions 52, 52 opposite to each other press areas on the body surface 12 which partially surround the protruding portion 36. However, in place of the sheet spring 48, it is possible to employ a disc spring adapted to contact and press a circular area on the body surface 12 which completely surrounds the protruding portion 36.

Although in the illustrated embodiment the pulse wave sensor 20 is adapted to be pressed by air pressure, it is possible to use an electrically driven feed screw to press the pulse wave sensor 20 on the body surface 12.

It is to be understood that the present invention may be embodied with other changes, improvements, and modifications that may occur to those skilled in the art without departing from the spirit and scope of the invention defined in the appended claims.

What is claimed is:

1. A pulse wave sensor for detecting a pressure pulse wave produced from an arterial vessel of a living subject in synchronism with heartbeat of the subject, the sensor having a press surface adapted to be pressed on a body surface of the subject over the arterial vessel, the sensor comprising:

means for providing a protruding portion protruding from said press surface, said protruding portion having a top surface adapted to be pressed on said body surface of said subject;

sensing means provided in said top surface of said protruding portion, for detecting said pressure pulse wave from said arterial vessel via said body surface; and a sheet spring provided around said protruding portion and having a height generally equal to, or greater than, a height of said protruding portion as measured from said press surface, said sheet spring being deflectable in a direction in which said top surface of said protruding portion is pressed on said body surface.

2. The pulse wave sensor as set forth in claim 1, wherein said sheet spring is linearly deflectable with respect to the pressing force applied thereto in said direction in which said top surface of said protruding portion is pressed.

3. The pulse wave sensor as set forth in claim 1, wherein said sheet spring includes at last one first portion and at least one second portion, said sheet spring being fixed at said first portion thereof to said press surface, said sheet spring being adapted to be pressed at said second portion thereof on said body surface of said subject, said second portion being deflectable relative to said first portion when being pressed on said body surface.

4. The pulse wave sensor as set forth in claim 3, wherein said sheet spring has a window formed therethrough at a central portion thereof, said protruding portion protruding through said window, said at least one first portion consisting of two first portions spaced apart from each other by said window in a first direction parallel to said arterial vessel with the pulse wave sensor being pressed on said body surface, said at least one second portion consisting of two second portions spaced apart from each other by said window in a second direction perpendicular to said first direction.

5. The pulse wave sensor as set forth in claim 4, wherein said sheet spring further includes two pairs of third portions, said two pairs being spaced from each other by said window in said first direction, the two third portions of each of said two pairs being continuous with a corresponding one of said two first portions located therebetween and with the corresponding ones of said two second portions, each of said two third portions of said each pair being bent from said corresponding one first portion at a predetermined angle with respect to said press surface.

6. The pulse wave sensor as set forth in claim 4, wherein said sheet spring further includes a curved portion extending from an outer periphery of each of said second portions toward said press surface, said press surface having a rounded outer periphery matched with a curvature of the two curved portions of said sheet spring, said two curved portions closely fitting over said rounded outer periphery of said press surface when said second and third portions o said sheet spring closely contact said press surface upon application thereto of an excessively large force between said press surface and said body surface.

7. The pulse wave sensor as set forth in claim 1, wherein said pressure sensing means comprises a plurality of pressure sensing elements formed in an array extending in a direction perpendicular to said arterial vessel with the pulse wave sensor being pressed on said body surface.

8. The pulse wave sensor as set forth in claim 1, wherein said means for providing said protruding portion comprises:

a support member from which said protruding portion protrudes, said support member including a portion thereof adapted to be secured to a device which operates for pressing the pulse wave sensor against said arterial vessel via said body surface; and a cover member covering said support member to provide said press surface, said covering member having a window through which said protruding portion protrudes from said support member.

* * * * *